US00RE36474E

United States Patent [19]

Stark

[11] E Patent Number: Re. 36,474

[45] Reissued Date of Patent: Dec. 28, 1999

[54] SIGNAL PROCESSING METHOD AND APPARATUS

[75] Inventor: Edward W. Stark, New York, N.Y.

[73] Assignee: Bionir, Inc., New York, N.Y.

[21] Appl. No.: 08/778,809

[22] Filed: Jan. 3, 1997

Related U.S. Patent Documents

Reissue of:

[64] Patent No.: 5,379,238
Issued: Jan. 3, 1995
Appl. No.: 07/923,029
Filed: Jul. 30, 1992

U.S. Applications:

[63] Continuation of application No. 07/815,640, Dec. 30, 1991, abandoned, which is a continuation of application No. 07/319,450, Mar. 3, 1989, abandoned.

[51] Int. Cl.[6] ..... A61B 5/00; G06F 15/42; G06G 7/48

[52] U.S. Cl. ..... 395/500.2; 356/39; 702/32; 600/322

[58] Field of Search ..... 364/498, 571.01, 364/571.02, 571.04, 571.05, 573, 574, 578; 128/633; 356/39, 40; 324/312, 322; 250/339.11, 339.12; 702/22, 23, 25, 30, 32, 85, 74, 77; 600/322

[56] References Cited

U.S. PATENT DOCUMENTS

| | | | |
|---|---|---|---|
| 4,014,321 | 3/1977 | March | 356/39 X |
| 4,017,192 | 4/1977 | Rosenthal | 356/39 X |
| 4,167,331 | 9/1979 | Nielsen | 356/39 |
| 4,412,341 | 10/1983 | Gersho et al. | 702/194 X |
| 4,791,577 | 12/1988 | Winter | 702/77 |
| 4,837,720 | 6/1989 | Rambaut | 702/74 |
| 4,863,265 | 9/1989 | Flower et al. | 600/322 |

*Primary Examiner*—William A. Cuchlinski, Jr.
*Assistant Examiner*—Edward J. Pipala
*Attorney, Agent, or Firm*—Schwegan, Lundberg, Woessner & Kluth, P.A.

[57] ABSTRACT

A method and apparatus for the determination of spectral samples is disclosed wherein spectral measurements are taken, normalization of the spectral measurements takes place, and a bilinear modeling is performed to extract spectral data. Once this data is derived, the interference quantitization levels are determined using multiple linear regression analysis, and are then removed from the sample readings in order to determine a more precise level of analyte spectra, such as analyte levels of glucose in serum or whole blood.

26 Claims, 3 Drawing Sheets

SIGNAL PROCESSING METHOD AND APPARATUS

Matter enclosed in heavy brackets [ ] appears in the original patent but forms no part of this reissue specification; matter printed in italics indicates the additions made by reissue.

This application is a continuation of application Ser. No. 815,640 filed Dec. 30, 1991 abandoned, which is a continuation of Ser. No. 319,450 filed Mar. 3, 1989, abandoned.

FIELD OF THE INVENTION

The present invention relates generally to processing of data signals to reduce undesired variations or noise present in the data. Specifically, the present invention relates to an instrument or method for processing of data signals to reduce undesired variations or noise present in data. Most specifically, the present invention relates to an instrument, method or process to provide measurements of analytes reduced from data by removing undesired variations and noise present in that data.

BACKGROUND OF THE INVENTION

Sensors are used to measure physical phenomena and to convert the measured values into data values. The magnitudes of these data values are presented as data signals. The measurement process itself will generally introduce errors and unwanted variations in the data values. In addition, additional errors and noise may be introduced in the conversion and transmission of data signals. In most cases, it is desired to extract from the data signals the data values associated with one or more "analytes", that is the magnitude of a specific physical phenomena. When a sequence of measurements is made, an additional dimension is added to the data signal structure, that is, an additional data point index is created relating the data values to the measurement sequence. For example, a single measurement, such as temperature, made at a sequence of times or on a series of specimens yields a stream of data values with one dimensional *data* point index. Two dimensional data point index structures result when each measurement in a sequence produces a "spectrum" consisting of multiple interrelated data values, such as an optical spectrum or a chromatogram.

Noise and variation in such data structures are often assumed to be random and unrelated among the data values . With such random data, the most direct approach to reducing variation and noise is in a weighted averaging of such data values. This is typically done by averaging the spectral data values of several spectra from the sequence of spectra, for instance, in combining measurements having the same spectral data point index, or "wavelength". Another typical approach is the weighted averaging the data values of several adjacent data points within each spectrum. In many instances, both types of averaging are often combined, to produce more precise measurements of data, and to further reduce effects of any variations or random noise in the data. Averaging assumes that no [interrelationship] *interrelationships* exist among the data values. If the data values are interrelated, there have also been developed a large number of multivariate methods of processing data signals to reduce noise and unwanted variations. In general, these methods are based on each data value containing several parts or components each related to a different physical phenomenon and, therefore, on each spectrum consisting of several "spectral components" characteristic of the associated physical phenomenon. Each spectral component consists of a set of data values and their associated data point indices. A spectral component may be represented by a data signal. These techniques have included, for example, such methods as least mean square methods of curve fitting various spectra. With this technique, each spectrum from the data set is approximated as a linear combination of the spectra of known constituents or components within the data. These approximations satisfy a least mean square criterion. The appropriate coefficients of these linear combinations are then linearly related with, typically, analyte concentrations in the specimens.

Curve fitting methods have been extended in various respects. First, multilinear correlation of several of the derived curve-fit coefficients with analyte values is accomplished to reduce the errors. Second, measured spectra from specimens of known compositions, rather than pure constituent spectra, are used as components. Errors are reduced using these techniques such that they become comparable to those obtained by multilinear regression using unmodified or derivative type data at selected wavelengths. Yet, such methods assume a previous knowledge of the reference spectra. As well, these methods are not applicable to situations where the interfering spectra have variable characteristics.

Other methods have included techniques such as spectral subtraction, where interferences are reduced by subtracting previously known or estimated reference spectra based on prior information about such spectra. For instance, in cases in which optical absorption spectra are used, it is known that such spectra will never be negative. Accordingly, once an absorption difference spectrum is estimated to be approximately *zero* at one or more data points, it is no longer desirable to subtract a greater interference magnitude from this spectrum. At that point, the combined interference spectrum is set, and the estimate of the analyte spectrum is obtained.

Other higher level techniques have included such methods as latent variable analysis or bilinear modeling. In these methods, underlying sets of data values, or latent spectra, are extracted statistically from a data set. These [method] *methods* include, among others, factor analyses, principal component analysis (PCA) and partial least square (PLS) methods. In these systems, a priori knowledge of the previously derived latent reference spectra are used as the spectral components throughout later analyses. In other words, once a latent reference spectral estimate is made, these higher level techniques inflexibly set the latent reference spectra.

All these previous techniques become inaccurate if the measuring instrument or conditions change significantly. In addition, these previous techniques are incapable of differentiating between the spectral component due to the mimicked analyte spectral component within the interference spectra. For instance, where interference spectral components of the data signal bear a correlation to the analyte spectral component, in many of the previous methods it is possible for the interference spectral component of the data signal to be confused with the analyte spectra, producing serious errors in the approximation techniques. Various methods have been proposed to correct these errors, but only after they have occurred.

SUMMARY OF THE INVENTION

Accordingly, it is an object of the present invention to determine the spectral components which interfere with measured data as these components are actually present in the data signals, rather than using a priori knowledge of these interfering components to fit the measured data for interference estimates and reduction.

It is a second object of the present invention to improve estimates of the interference spectra by removing intercorrelation between *the* analyte spectral data values and interference spectral data values in the data signals.

It is a third object of the present invention to improve estimates of the degree of interference, independent of analyte and interference concentrations in the data signals, by removing intercorrelations between the analyte spectral data values and interference spectral data values within the data signals [spectra].

It is yet another object of the present invention to correct interferences within the data signals by a more accurate determination of the character and magnitude of these interferences.

It is an additional object of the present invention to subtract interference spectral component data values from the measured data values based on the improved estimates of the character and magnitude of the inference signal components and eliminate these interferences substantially completely from the measured data to improve the ultimate determination of analytes within the originally measured data.

Finally, it is an object of the present invention to incorporate the more accurate measurements of desired data values through subtraction of these interference spectral component values in a method and apparatus for accurate measurements of analytes. It is most desireable to incorporate these methods and apparatus in an apparatus to measure analyte levels, including such methods as taking near infrared measurements of analyte levels in blood, especially the measurement of glucose levels in whole blood or blood products.

These and other objects of the present invention are accomplished in a method wherein spectral characteristics *of* interferences are not considered a priori information, but are derived from data signals as they are being measured, using bilinear modeling, on a *set* of data values [set] consisting of one or more replicate groups of spectral signals. That is groups of spectral signals for which the analyte magnitude is substantially constant within each replicate group of spectral measurements. The replicate group average spectral signal of each replicate group is subtracted from each spectral signal within the group. Within each replicate group, the analyte spectral signal is constant, and will be contained in the average spectral signal which is subtracted. Once the appropriate replicate group average spectrum is subtracted, data values from [,] multiple replicate groups of spectral signals may be combined into a larger data set for the bilinear modeling to determine latent variable interference spectral data values. Thus, the components of the bilinear model are derived from the set of modified spectral data values, after removal of the replicate group average spectral data values from each set of spectral data values in each replicate group of spectral data values. These [will] spectral component data values will be used to explain variance in the measured data. Even if the analyte concentration changes between the replicate groups[,] of measurements, the analyte variance is zero, because the analyte signal has been removed by subtracting the replicate group average spectral signal. Thus, the bilinear modeled component data [valued] *values* represent the spectra of variable interferences and do not include significant analyte information.

Despite the removal of the analyte signal from the data signal prior to bilinear modeling, the resultant latent variable interference spectral data values will usually be correlated to some degree to the analyte spectral shape. This correlation could cause errors in estimating the magnitude of each interference. Therefore, the [spectrum] *spectral data values* of each of the interferences, whether known a priori or derived, is projected on the analyte spectral data values to find the portion of each interference which is unique, i.e., orthogonal to the analyte spectrum. Each interference spectrum will be equal to the sum of its unique portion and a certain amount matching or mimicking the analyte spectrum in spectral characteristics. Projection of each measured spectrum on the unique portions of the interferences (for instance by regression analysis) provides coefficients to represent an estimate of the amount of each interference present in each measured spectrum.

Each set of spectral data values for the unique interference portion is orthogonal to the set of analyte spectral data values. Thus, these estimates of interference magnitude are not biased by the analyte concentration. For each interference, the coefficients of the unique portion can be applied to the original spectral data values of the interference to determine the amount of that interference spectral signal to subtract from the measured spectral data in order to eliminate that portion of the interference. To insure that the measured spectral data are replicates with respect to the analyte, the present invention may include a step of normalizing the measured spectral intensity so that the analytes' spectral signal is kept constant for constant analyte concentration.

These and other objects of the present invention are accomplished in connection with the following discussion the drawings as well as a detailed description of the inventions in which:

DETAILED DESCRIPTION OF THE DRAWINGS

DETAILED DESCRIPTION OF THE PRESENT INVENTION

The present invention has general applicability in the field of signal and data processing, wherever a sequence of "spectra" or data structures consisting of multiple interrelated data values, are obtained and the desired variability in the data can be described as "spectral" patterns. One dimension of the two dimensional data structure [can be] *is* considered a "sequence", with the other dimension representing the data point indices of the spectra. In these cases, which are the rule rather than the exception, this method is effective in reducing unwanted variability and noise.

As an example, optical spectroscopy, for instance, in the determination of analyte levels in blood using near infrared techniques, often exhibits interferences which change from measurement to measurement due to unavoidable changes in the measurement geometry, the composition of matrix surrounding the analyte, or physical factors such as bulk density, scattering, temperature, bubbles, cavitation, other flow effects, and similar phenomena. Such problems are common in regular transmission, diffuse reflection, diffuse transmission and interaction measurements. The precision of on-line process control measurement of clear liquids is usually limited by variable compositional or physical interferences rather than truly random noise.

Figure 1:
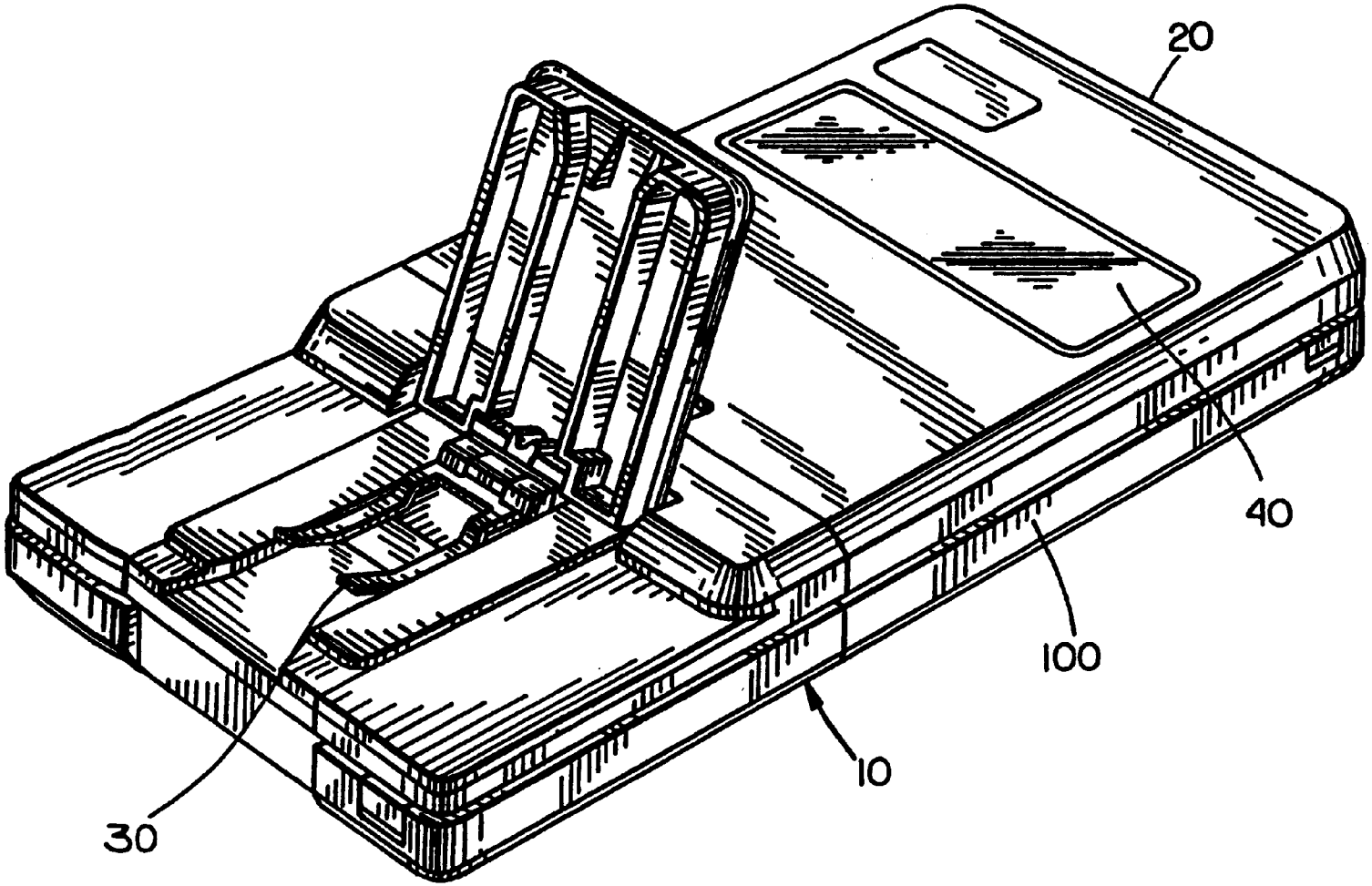
FIG. 1 is a perspective view of a spectrophotometric sensor system for use in performance of the methods and apparatus of the present invention.
Figure 2:
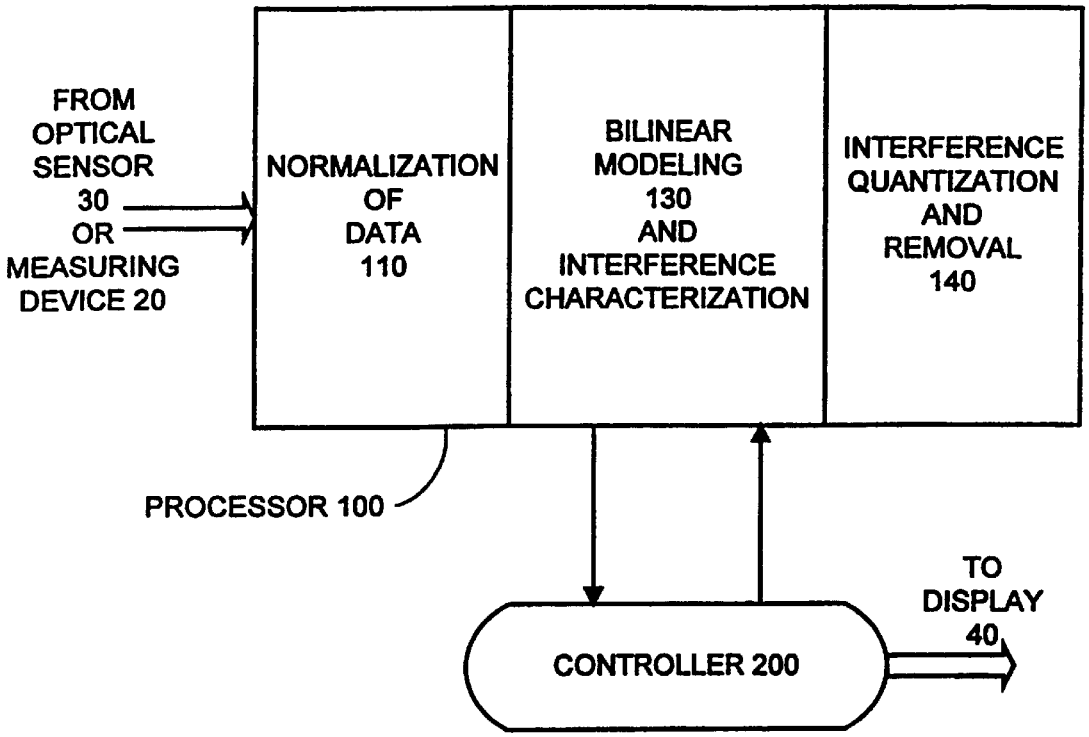
FIG. 2 is a general block diagram of the apparatuses used as components in conjunction with the present invention as shown in FIG. 1.

As can be seen from FIG. 1, for instance, a spectrophotometric sensor system 10 as used in the present invention is described. This system can be used, for instance, in the determination of analyte levels in blood or, for instance, in the display of glucose levels in blood. This sensor system 10 comprises a measuring device 20 with an optical sensor 30 which will *give* data signals corresponding to [give] optical readings of spectral data values, [,] for instance, spectrophotometric measurements of specimens or materials such as blood. From this measuring device 20 the processor 100 used in conjunction with the method of the present invention is attached. This can be seen in FIG. 2. From the processing unit 100, a controller/analyzer 200 is attached, which allows the processed data to be analyzed and the processing unit 100 is to be controlled based on the data analysis results. The data, after analysis, is sent to display 40.

The processor 100 of the present system follows a five-step approach: a) The processor 100 takes the specimen-derived spectral data from the measuring sensor device 20 and normalizes the data. b) After this optional normalization, the processor extracts the data values for the variable interference spectral components from the data signals. c) The data values of these components are then separated by regression with the analyte spectral data values to remove the portion of the interference signal which mimicks the analyte signal. d) The magnitudes of the interferences are determined by multiple regression of the data values of each measured spectrum on the data values of *these* analyte-orthogonal interferences. Finally, e) the originally extracted interferences are scaled by these magnitudes and subtracted from the original normalized data values in order to finally provide [a] corrected spectral *data values* for use in controller/analyzer 200 to determine the analyte levels. It is these which are ultimately displayed in the display unit 40 of the system 10. If desired, steps c) through e) can be repeated for additional analytes.

The present application now turns to the five distinct functions taking place in the processing unit 100 of the system. Each of the measured spectra, $S_n$, is sequentially stored in the group storage area 112 of the normalizing portion 110 of the processor 100. From this group storage area 112, each set of the spectral data values $S_n$ from a replicate group is added together and divided by the number of measurements in the group in order to determine the average spectral data values, $\bar{S}$, at averager 115.

Thus, the [spectra] *spectral data values* can be described as in equation (1) below:

$$[S_n = b_{on} + b_{on} + b_{ln}\bar{S} + S'_n]\ S_n = b_{0n} + b_{1n}S + S'_n \tag{1}$$

In equation (1), $S'_n$ is described as variations in individual spectra from the average spectrum, $\bar{S}$. The coefficient [$b_{on}$] $b_{0n}$ represents an additive offset in the measured spectral data, and the coefficient [$b_{ln}$] $b_{1n}$ corresponds to a multiplicative scale factor relating spectrum $S_n$ to the average spectrum.

[A normalized] *Normalized* or corrected spectral data values[;] $\hat{S}_n$ are then derived using equation (3) in the adder/divider element 116 of the normalization unit 110:

$$\left[\hat{S} = \frac{S_n - b_{on}}{b_{ln}}\right]\ \hat{S} = \frac{S_n - b_{0n}}{b_{1n}} \tag{3}$$

From equations (3) and (1), showing $$\left[\hat{S}_n = \bar{S} + \frac{S'_n}{b_{ln}}\right]\ \hat{S}_n = \bar{S} + \frac{S'_n}{b_{1n}}$$

that all the differences, $S'_n$, from the average have been normalized by the factor [$b_{ln}$] $b_{1n}$. In order to further proceed toward the ultimate determination of analyte levels, spectral data values describing the interferences should be extracted, but only on variable components, and not on components to be determined, such as analyte levels. Therefore, the newly derived $\hat{S}_n$ are once again grouped in the group storage unit 132 of the interference characterization section 130 of the processor 100. From this replicate group data an average, $\hat{S}_{avg}$, is taken. Then, each $\hat{S}_n$ has subtracted from it the $\hat{S}_{avg}$ to arrive at a newly derived $\hat{S}'_n$ as in equation (6):

$$\hat{S}'_n = \hat{S}_n - \hat{S}_{avg} \tag{6}$$

Now each of the newly derived $\hat{S}'_n$ will not contain any contributions from the desired analyte spectral data signals.

As each individual $S'_n$ is derived, it is stored in the combined group storage unit 134 in the interference characterization portion 130. Once a desired number of replicate groups of $\hat{S}'_n$ data are stored, they are used as a set within the components analyzer 136. In using known methods of bilinear modeling such as PCA, the set of spectral data $\hat{S}'_n$ are analyzed and broken into components [$P_l$–$P_j$] $P_1$ *to* $P_j$. It is known, however, that each of these components [$P_1$–$P_j$] $P_1$ *to* $P_j$ are mutually orthogonal.

Thus, the derived $P_j$ components data are now ready for input into the interference quantization and removal area 140 of processor 100. In most instances, the spectrum of the derived components $P_j$, will have some similarity to the known spectrum of the analyte, for instance, glucose. In these cases, the correlation between the two spectra will not equal zero, and regressing of the spectral data $\hat{S}_n$ on the interfering components $P_j$ would produce incorrect coefficients influenced by analyte concentration. Thus, the derived components must be modified in order to appropriately orthogonalize these components with respect to the analyte. This is accomplished by removing the entire portion of the interference (component spectrum $P_j$) which mimics the analyte.

Thus, the individual derived component data values, $P_j$, are put into a simple linear regression analyzer 142. Data values of each component $P_j$ are projected on the data values of known analyte reference spectrum, A, from reference area 141. After the linear regression is accomplished, coefficient data values quantifying the analyte like portion [$c_j$] $c_{ij}$ are derived for each individual component $P_j$.

These coefficient data values [$c_j$] $c_{ij}$ are multiplied by the known analyte [spectrum] *spectral data values* A to determine the portion of each component spectral data [$P_j$which] $P_j$ *which* mimics the analyte spectral data A. Thus, a modified spectral principal component $Q_j$ can be derived at combiner 143 [at] for each $P_j$ as in equation (7):

$$Q_j = P_j - [c_j]c_{ij}A \tag{7}$$

Importantly, each $Q_j$ will now be orthogonal to the analyte spectrum A. As a check on these operations, coefficient [$C_{oj}$]$C_{0j}$ should be derived, where [$C_{oj}$] $C_{0j}$ should equal zero.

Now, the previously stored corrected individual [spectra] *spectral data* $\hat{S}_n$ can be analyzed using the modified components data $Q_j$ in order to determine the magnitude of each component $Q_j$ spectral signal contained in each group corrected individual *spectral signal* $\hat{S}_n$. As seen in the interference quantization and removal section 140, a multiple linear regression analysis at analyzer 144 is performed regressing [each] the data values of *each* $\hat{S}_n$ on the data values of $Q_j$ components to arrive at coefficient data values $m_{jn}$ where each of the $m_{jn}$ conforms to equation (8):

$$\hat{S}_n = m_{on} + \sum_j m_{jn} Q_j + \epsilon \tag{8}$$

As seen in equation (8), the [$m_{0n}$] $m_{on}$ are described as offsets of the spectral data.

Now data values of the newly derived factors $m_{jn}$ can be combined with the data values of the components $P_j$ at multiplier 145 in order to determine the actual interference component [spectra,] *spectral data values* data values $I_{jn}$, in each specimen, according to equation (9):

$$I_{jn} = m_{jn} P_j \tag{9}$$

Figure 3:
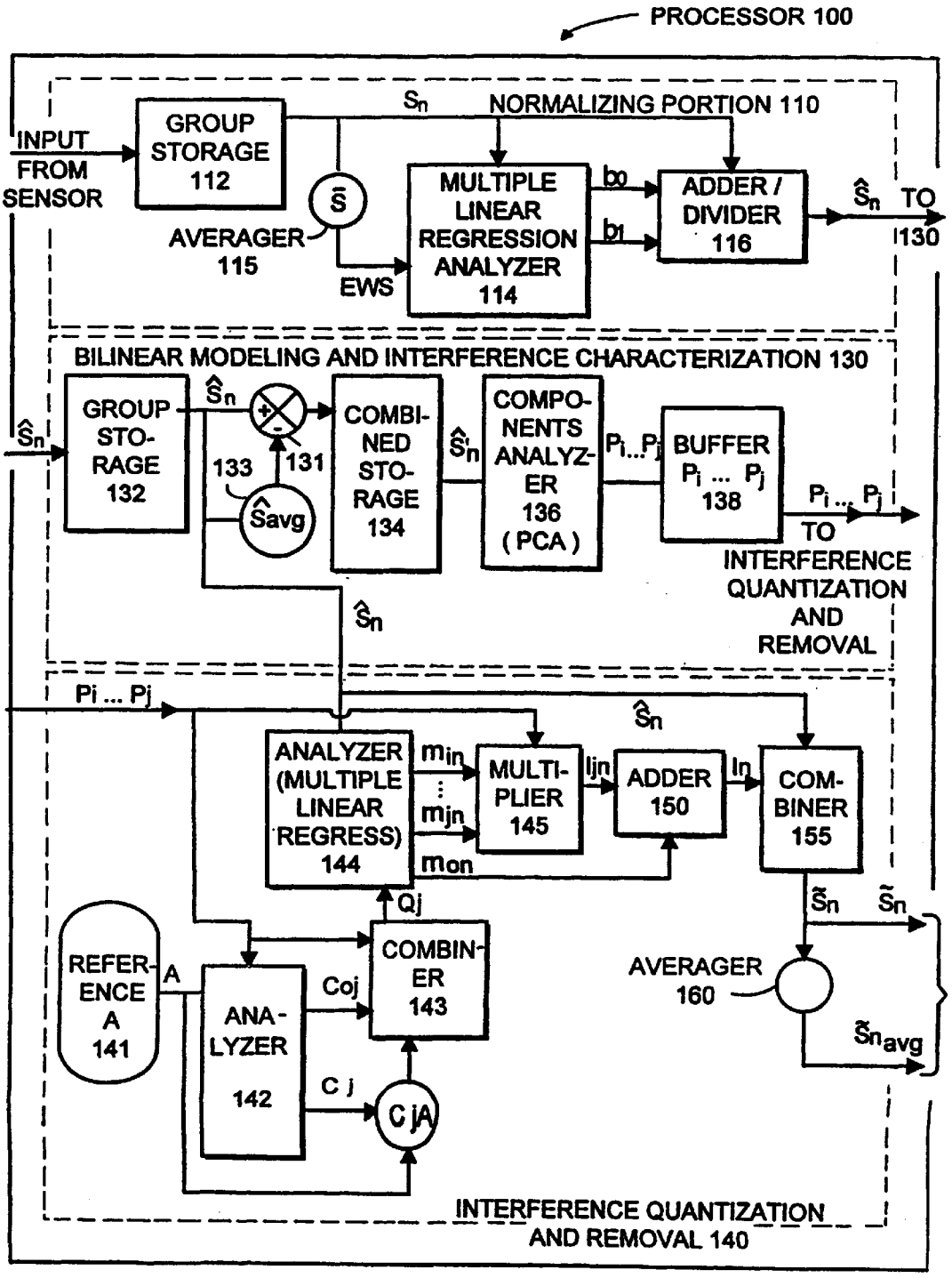
FIG. 3 is a block diagram of the processor unit as used in the present invention.

One remaining step is necessary to determine the entire interference spectral signal contained in the spectral signal of [specimen] each *specimen*. Thus, each individual interference component, $I_{jn}$, is placed into a vector adder 150 as seen in FIG. 3. The corresponding data values of each of the interference components is summed. The offset data value m is added on to this factor according to equation (10):

$$I_n = m_{on} + \sum_j I_{jn} \tag{10}$$

Now, the interference spectral data values derived for each specimen, $I_n$, can be removed from the corrected individual [ spectra $S_n$] *spectral data values* $\ddot{O}_n$. At combiner 155, as in equation (11), the sum of the interference components, $I_n$, is subtracted from the corrected individual [spectra $S_n$] *spectral data values* $\ddot{O}_n$ to arrive at the final corrected spectral data $\overline{S}_n$:

$$\overline{S}_n = \hat{S}_n - I_n \tag{11}$$

Of course, in order to more clearly approximate the $\hat{S}_n$ and reduce residual random errors, an average can be taken at averager 160 in the final step of the interference quantitization and removal process. Thus, the newly arrived average final corrected spectral data $\tilde{S}_{navg}$ will most accurately parallel the level of analyte that is present in the specimen.

Optionally, it is possible to use a buffer 138 as seen in the same step in order to prevent changes in analyte levels within a replicate group from causing errors. For instance, in cases where a presumed constant analyte level actually changes, these changes can be monitored by controller/analyzer 200 using the output signal $\tilde{S}_n$. If the analyte *signal* variation within a replicate group of [measurement] *measurements* is larger than a predetermined amount, the [inference] *interference* component data values derived during the present derivation are determined to be inaccurate, and previously stored ones are used.

While the present application has been described in connection with a presently preferred embodiment, it will be recognized that the invention is to be determined from the following claims and their equivalents.

What is claimed is:

1. In a method for determining analyte levels for displaying glucose levels in blood using near infrared techniques including the steps of:

measuring glucose levels of a parameter related to blood using near infra-red optical techniques to provide a set of signals representing spectral data, said spectral data including spectral components resulting from physical properties of an environment in which measurement takes place which components interfere with the measured data; and processing said [spectra-representing] signals *representing spectral data* having said interfering spectral components by:

removing the effect of constant analyte contribution by subtracting signals representing average spectra of replicate groups of said spectral data to form signals representing modified spectra representing variable interference information;

determining signals representing component spectra of said modified spectral signals by bilinear model analysis;

determining signals representing the magnitude of each said component spectra contained in each original spectrum and [applying these signals representing magnitudes to signals representing component spectra] *multiplying these signals representing component spectra by data values of signals representing magnitudes* to develop signals representing interference spectra; and removing said signals representing the resulting interference spectra from said signals representing said original spectra for producing corrected spectral signals representing said spectral data of glucose blood levels with said interference components removed.

2. Apparatus for processing signals representing measured spectral data for removing effects of spectral components which interfere with said measured data in determining analyte levels and in displaying glucose levels in blood using near infrared techniques comprising:

means for measuring glucose levels of a parameter related to blood using near infrared optical techniques to provide a set of signals representing spectral data, said spectral data including spectral components resulting from physical properties of an environment in which measurement takes place which components interfere with the measured data;

means for processing said spectra-representing signals having said interfering spectral components including:

a subtractor for removing the effect of constant analyte contribution by subtracting signals representing [the] average spectra of replicate groups of said spectral data to form signals representing modified spectra representing variable interference information;

a components analyzer for determining representative signals of component spectra of said modified spectra by bilinear model analysis;

an analyzer for determining signals representing the magnitude of each said component spectra contained in each original spectrum and [means for applying these magnitude-representing signals to the component spectra] *a multiplier for multiplying data values of said representative signals of component spectra by data*

*values of said signals representing the magnitude of each said component spectra* to develop signals representing interference spectra; and a combiner for removing said signals representing the resulting interference spectra from said signals representing said original spectra for producing corrected spectral signals representing said spectral data of glucose blood levels with said interference components removed.

*3. A method for processing signals representing measured spectral data obtained from a sensor that measures physical phenomena, said measured spectral data including a desired spectral data component and interference spectral data components which interfere with the desired spectral data component, in order to remove effects of said interference spectral data components thereof which interfere with said desired spectral data component, said method comprising the steps of:*

*combining interference component spectral signals representing said interference spectral data components and a reference spectral signal representing reference spectral data by means of linear modeling to modify said interference component spectral signals such that they represent modified interference component spectral data which are orthogonal with respect to said reference spectral data;*

*analyzing signals representing each individual spectrum of said measured spectral data by linear modeling with respect to said signals representing these modified, reference-orthogonal interference spectral data components to determine the magnitude of each said modified, reference-orthogonal interference spectral data component comprising said individual spectrum of said measured spectral data and providing representative signals thereof;*

*using signals representing said magnitudes to scale the magnitude of the signals representing the original unmodified interference spectral data components, and removing said scaled signals representing the interference spectral data components from signals representing said each individual spectrum of said measured spectral data thereby producing corrected signals representing said measured spectral data with said interference spectral data components removed.*

*4. The method of claim 3 wherein said reference spectral data is representative of said desired spectral data component.*

*5. The method of claim 3 wherein the interference component spectral signals are derived by performing bilinear model analysis on signals representing spectral data that comprise little or none of said desired spectral data component.*

*6. The method of claim 5 wherein said signals representing spectral data that do not include said desired spectral data component are derived from the measured spectral data, said method comprising the additional steps of:*

*averaging spectral data from signals representing groups of said measured spectral data and providing signals representing said group average spectral data;*

*subtracting said signals representing said group average spectral data from said signals representing said measured spectral data to produce signals representing modified spectral data comprising variability of each spectrum of said measured spectral data from said group average spectral data; and*

*taking said signals representing at least one of said groups of said modified spectral data and performing bilinear model analysis to develop interference component spectral signals comprising said signals representing modified spectral data.*

*7. The method of claim 3 wherein said interference component spectral signals are known a priori on the basis of previous measurements.*

*8. The method of claim 3 wherein said physical phenomena comprise electromagnetic radiation.*

*9. The method of claim 3 wherein said corrected signals provide signals of the magnitude of physical phenomena related to the desired spectral data component.*

*10. A method for processing signals representing measured spectral data obtained from a sensor that measures physical phenomena, which data include an analyte spectral data component, in order to reduce any effect of interference spectral data components thereof which interfere with said analyte spectral data component, said method comprising the steps of:*

*removing analyte spectral data component effects from measured spectral data to form signals representing modified spectral data representing variable interference spectral data;*

*determining signals representing interference spectral data components of said modified spectral data by bilinear model analysis;*

*determining signals representing the magnitude of each said interference spectral data component contained in each original spectrum of said measured spectral data and using these magnitude-representing signals to scale said signals representing interference spectral data components to develop signals representing the scaled interference present within each original spectrum of said measured spectral data; and*

*removing the signals representing said scaled interference spectral data components from the signals representing said original measured spectral data for producing corrected signals representing the measured spectral data with the interference spectral data components removed.*

*11. The method of claim 4 wherein the signal representing each said interference spectral data component contained in each original spectrum of said measured spectral data is combined with signals representing known reference spectral data to modify each said interference spectral data component to provide representative signals which are orthogonal to the signals representing said known reference spectral data and wherein the signals representing each original spectrum of said measured spectral data are analyzed to determine signals representing the magnitudes of each modified, reference orthogonal interference spectral data component contained therein and then these magnitude representing signals are used to scale said signals representing the original interference spectral data components to develop signals representing the scaled interference spectral data components present within each original spectrum of said measured spectral data.*

*12. The method of claim 11 wherein said combining step and said analyzing step are performed by linear modeling.*

*13. The method of claim 11 wherein said interference spectral data components determined by bilinear analysis are designated $P_j$ and wherein said combining step includes performing linear regression analysis by projecting a signal representing each interference spectral data component on a signal representing known analyte spectral data A and developing signals representing coefficients quantifying the analyte-like portion $c_{ij}$ for each individual interference spectral data component $P_j$; multiplying the signals repre-*

*senting coefficients $c_{ij}$ by the signal representing the known analyte spectral data A to determine the portion of each interference spectral data component $P_j$ which mimics the analyte spectral data A to develop a signal representing a modified interference spectral data component $Q_j$ for each $P_j$ so that*

$$Q_j=P_j-c_{ij}A.$$

*14. The method of claim 13 wherein the groups of modified spectral data are designated as $\hat{S}_n$, the analyzing step employs signals representing said modified interference spectral data components, $Q_j$, to determine a signal representing the magnitude of said modified interference spectral data components, $Q_j$, in each group of modified spectral data, $\hat{S}_n$, by performing multiple linear regression analysis by regressing each $\hat{S}_n$ on said modified interference spectral data components to develop signals representing coefficients $m_{jn}$, where each $m_{jn}$ is related by*

$$\hat{S}_n=m_{on}+{}_j\Sigma m_{jm}Q_j+\epsilon,$$

*$m_{on}$ being the offsets of the spectral data; and*

*by combining the signals representing $m_{jn}$* coefficients with signals representing components $P_j$ *to determine signals representing the actual interference spectral data component, $I_{jn}$, in each spectrum of said measured spectral data according to the relationship*

$$I_{jn}=m_{jn}P_j.$$

*15. The method of claim 14 further comprising the step of adding signals representing the individual interference spectral data components with a signal representing the offset $m_{on}$ to develop a signal representing the interference spectral data in accordance with the relationship*

$$I_n=m_{on}+{}_j\Sigma I_{jn};$$

*and wherein a signal representing the final corrected spectral data, $\tilde{S}_n$, is developed by removing the interference spectral data according to the relationship*

$$\tilde{S}_n=\hat{S}_n-I_n.$$

*16. The method of claim 11 wherein said signals of the analyte concentrations are displayed.*

*17. The method of claim 10 wherein the signals represent the magnitude of each interference spectral data component contained in each original spectrum of said measured spectral data are determined using signals representing known reference spectral data and the measured spectral data in a bilinear model.*

*18. The method of claim 10 further comprising the step of normalizing the signals representing the measured spectral data by correcting for offsets and multiplicative errors using coefficients determined by linear modeling.*

*19. The method of claim 18 said method further comprising the step of normalizing the measured spectral data, $S_n$, said step of normalizing the measured spectral data comprising the steps of:*

*adding signals representing said measured spectral data, $S_n$, together;*

*dividing the sum of said representative signals by the number of signals added together to form signals representing average spectral data, $\bar{S}$; and*

*forming a signal representing modified spectral data $\hat{S}_n$ based on the relationship*

$$\hat{S}_n=\bar{S}+(S_n'/b_{1n});$$

*where $b_{1n}$ corresponds to a multiplicative scale factor relating $S_n$ to the average spectral data, $\bar{S}$, and where $S_n'$ represents variations in individual spectra of the measured spectral data from the average spectral data, $\bar{S}$.*

*20. The method of claim 10 wherein said physical phenomena comprise electromagnetic radiation.*

*21. The method of claim 10 wherein said signals of said magnitude of physical phenomena are displayed.*

*22. The method of claim 10 wherein said corrected signals provide signals of the analyte concentrations.*

*23. The method of claim 10 wherein constant analyte spectral data component efforts are removed from said measured spectral data by subtracting signals representing average spectra of replicate groups of said measured spectral data from said signals representing measured spectral data.*

*24. An apparatus for processing signals representing measured spectral data for removing effects of spectral data components which interfere with said measured spectral data, said apparatus comprising:*

*a subtractor for removing constant analyte spectral data effects by subtracting signals representing the average spectral data of replicate groups of said measured spectral data to form signals representing modified spectral data representing variable interference information;*

*a components analyzer for determining representative signals of component spectral data of said modified spectral data by bilinear model analysis;*

*an analyzer for determining magnitude-representing signals representing the magnitude of each said component spectral data contained in each original measured spectral data and a multiplier for using these magnitude-representing signals to scale said component spectral data to develop signals representing interference spectral data; and*

*a combiner for removing signals representing the resulting interference spectral data from signals representing said original measured spectral data for producing corrected spectral signals representing said measured spectral data with said interference components removed.*

*25. The apparatus of claim 24 wherein said analyzer includes:*

*means for combining signals representing of said component spectral data with signals representing known reference spectral data to modify said component spectral signals such that they are orthogonal to the signals of the known reference spectra and*

*means for analyzing each signal representing the original measured spectral data to determine signals representing the magnitudes of each modified, reference-orthogonal component contained in them for then using these magnitude-representing signals to scale the original component spectral data to develop signals representing interference spectra.*

*26. The apparatus of claim 24 wherein said apparatus includes a sensor that measures physical phenomena and provides signals representing measured spectral data.*

* * * * *